US006299892B1

(12) United States Patent
Schmitz

(10) Patent No.: US 6,299,892 B1
(45) Date of Patent: *Oct. 9, 2001

(54) COMPOSITION OF MATTER HAVING BIOACTIVE PROPERTIES

(76) Inventor: Robert A. Schmitz, 111 Brookside Dr., Greenwich, CT (US) 06831

( * ) Notice: Subject to any disclaimer, the term of this patent is extended or adjusted under 35 U.S.C. 154(b) by 0 days.

This patent is subject to a terminal disclaimer.

(21) Appl. No.: 07/839,409

(22) Filed: Feb. 20, 1992

Related U.S. Application Data

(63) Continuation-in-part of application No. 06/934,689, filed on Nov. 25, 1986, now abandoned, which is a continuation-in-part of application No. 06/825,400, filed on Feb. 3, 1986, now abandoned.

(51) Int. Cl.[7] ..................................................... A01N 25/12

(52) U.S. Cl. .......................... 424/405; 524/379; 523/340; 523/122

(58) Field of Search ................................ 424/78.37, 405; 521/39; 528/232, 248, 254, 256, 258, 265, 501, 491, 492; 523/208, 340; 524/492, 379, 386; 525/398, 509

(56) References Cited

U.S. PATENT DOCUMENTS

| | | | | |
|---|---|---|---|---|
| 2,097,439 | * | 11/1937 | Beutner | 424/78.37 |
| 2,961,373 | * | 11/1960 | Boyer | 424/78.37 |
| 3,016,327 | * | 1/1962 | Schmitz et al. | 424/78.1 |
| 3,062,710 | * | 11/1962 | Moyle et al. | 424/78.37 |
| 3,081,221 | * | 3/1963 | Moyle et al. | 424/78.37 |
| 3,102,107 | * | 8/1963 | Aebi et al. | 424/78.37 |
| 3,130,193 | * | 4/1964 | Shaw | 544/181 |
| 3,215,596 | * | 11/1965 | Moyle et al. | 424/78.37 |
| 3,223,513 | * | 12/1965 | Geary | 424/78.37 |
| 4,160,754 | * | 7/1979 | Lehapel et al. | 524/765 |

FOREIGN PATENT DOCUMENTS

| | | | | |
|---|---|---|---|---|
| 573116 | * | 11/1945 | (GB) | 521/39 |

* cited by examiner

*Primary Examiner*—Peter F. Kulkosky
(74) *Attorney, Agent, or Firm*—Philip M. French

(57) ABSTRACT

Particles of coordinated complex comprising a basic, hydrous polymer and a capacitance adding compound, as well as methods for their production, are described. These complexes exhibit a high degree of bioactivity making them suitable for a broad range of applications through their incorporation into conventional vehicles benefiting from antimicrobial and similar properties.

24 Claims, No Drawings

COMPOSITION OF MATTER HAVING BIOACTIVE PROPERTIES

RELATED APPLICATIONS

This application is a continuation-in-part of abandoned application Ser. No. 06/934,689 filed Nov. 25, 1986; which is a continuation-in-part of abandoned application Ser. No. 06/825,400 filed Feb. 3, 1986.

FIELD OF THE INVENTION

This invention relates broadly to bioactive compositions of matter and to methods for preparing those compositions of matter. More particularly, this invention relates to biocidal or antimicrobial compositions of matter for use in consumer and health care products such as soaps, detergents, surgical scrubs, antimicrobial handwashes, and the like, wherein the active agent is a dispersion of particles of coordinated complex of basic, hydrous polymer and a capacitance adding composition. This invention further relates to methods for preparing those dispersions and incorporating them into a range of delivery vehicles suitable for effecting the desired antimicrobial end use.

BACKGROUND OF THE INVENTION

Numerous bioactive materials are available commercially. They are conventionally incorporated in a variety of vehicles and are used as preservatives in personal care products, in drugs, in household and industrial products such as paints, fuels, and the like, and in other compositions wherein their effect is sought. Other bioactive materials are used for disinfecting surfaces. These include room disinfectants, detergent compositions, and the like. Still other such materials find important agricultural purposes such as pesticides.

The use of polymers for bioactive applications is not broadly new. With respect to the present invention, reference is made to applicant's U.S. Pat. No. 3,016,327, issued Jan. 9, 1962, which is incorporated herein by reference. See also U.S. Pat. No. 2,428,329 (Ham, Sep. 30, 1947) (cited in U.S. Pat. No. 3,016,327); U.S. Pat. No. 3,102,108, (Ed. Geistlich Soehne AG, Aug. 27, 1963); J. R. Woodward and M. S. Korczynski, "Applications of a Halogen-Resin Complex in Water Purification", Chapter 45 in *Developments in Industrial Microbiology,* Volume 14. Washington, D.C.: American Institute of Biological Sciences, 1973; U.S. Pat. No. 3,428,607 (Renner, Feb. 19, 1969); U.S. Pat. No. 4,071,670 (Vanzo and Lewis, Jan. 31, 1978); U.S. Pat. No. 3,928,272 (Brancato and Herman, Dec. 23, 1975); and German Patent Application DE 2831192 (Pfaudler-Werke AG, Jan. 1, 1980).

U.S. Pat. No. 3,102,108 describes bacteriostatic polymers, especially urea-formaldehyde condensates. They are said to take the form of substantially linear chains, possibly lightly cross-linked. The patent indicates that many of the nitrogens of urea formaldehyde condensates form hydroxymethylene groups and that the presence of those groups is reflected in the properties of the products.

The bacteriostatic products of U.S. Pat. No. 3,102,108 are prepared by condensing urea and formaldehyde under alkaline conditions and then spraying the condensate through a rotary nozzle into a drying tower at elevated temperatures to form a condensation product in the form of a white powder. That powder is used as a dusting powder in ointments, suspensions, or in tablets.

Schmitz et al., U.S. Pat. No. 3,016,327, describes germicidal compositions comprising solid or liquid soap or nonionic detergent containing active biocidal agent, the latter being colloidal particles of an alkali-activated or basic anion-exchange resin which is preferably a urea-guanidine-formaldehyde condensate. In the patent, the colloidally sized particles of polymer are prepared by procedures known in the art such as, for example, the methods of U.S. Pat. Nos. 2,251,234 and 2,285,750 and in U.S. Pat. No. 2,434,190. These methods relate to the preparation of water insoluble, anion-active resins, the molecular weight of which is a function of the degree of condensation and cross linking. It is said to be critical to reduce the resin prepared in the condensation reaction to a colloidal size in order to effectively disperse the material in a vehicle and to insure that the desired germicidal phenomena take place.

In the patent, polymer syrup formed under alkaline conditions is acidified under constant agitation to a pH of 4. The acidified product is slowly cooled, during which time transition into the gel state is initiated due to the acidification, and proceeds to completion. At room temperature, the acidified gel continuum is broken up into granules of approximately 8 mesh. The granules are oven-dried first at about 55° C. for 6 hours, and finally at 100° C. for 1 hour. The dried, hardened, mechanically rigid anion-exchange resins are ground and treated with an alkaline solution. The pH adjusted "alkali activated" anion-active resin granules are then washed, separated by filtration, and oven-dried, before being micropulverized. Finally, the micropulverized resin particles are passed through a micro-atomizer. The resultant product may then be incorporated into any number of vehicles for its ultimate use.

SUMMARY OF THE INVENTION

It is a primary object of this invention to prepare bioactive compositions of matter for various end uses, which compositions are reliable, and effective.

It is a further and primary object of this invention to provide bioactive compositions of matter for various end uses, including products for topical application in large volume consumer and health care products such as soaps, detergents, surgical scrubs, and antimicrobial handwashes, which are cost effective and have broad spectrum activity against bacteria and other harmful natural protein substances.

It is a related and important object of this invention to provide bioactive compositions for topical application which are substantive to keratinous and cellulosic substrates and have long term effectiveness.

It is still a further object of this invention to provide bioactive polymer systems which are compatible with a multiplicity of delivery vehicles.

It is a further and primary object of this invention to provide bioactive compositions substantially no larger than 2000 nanometers which are able to be contained within the boundaries of colloidally dimensioned aqueous vapors, mists, aerosols, soap films, foams, and emulsions.

It is still a further object of this invention to provide methods for forming bioactive compositions of matter and for forming the ultimate end use products incorporating those compositions of matter which are simpler, more reliable, and less expensive than the methods employed in the art.

These and other objects of the invention are achieved in compositions of matter comprising particles of a coordinated complex of certain condensation polymers with a capacitance adding compound wherein substantially all of the particles are less than 2000 nm in diameter.

The polymer of these compositions is a basic, hydrous condensation polymer formed from at least two primary constituents: a carbonyl compound and a reactive monomer. The polymer may include other monomer, especially monomer which is reactive with the N-hydroxymethylene groups formed by the primary constituents. The resultant polymers naturally contain entrained and bound water produced as a by-product of their condensation. A capacitance adding compound is dielectric material having available electrons for coordination complexing with these low molecular weight polymers. Upon combination, the polymer and capacitance adding compound form a novel complex possessing extraordinary degrees of bioactivity.

DETAILED DESCRIPTION OF THE INVENTION

Preferred condensation polymers of this invention are condensed from (1) a monomer selected from compound having the formula

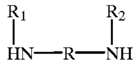

wherein R is >C═NH, —[$(CH_2)_m NH(CH_2)_o$]p— and —$(CH_2)$—$_n$ where m, o, and p are zero or an integer from 1 to 4, and at least one of m or o is an integer, n is an integer from 1 to 6, and $R_1$ and $R_2$ are H or alkyl or alkenyl or acyl or aryl or melamine or guanamine or piperazine, and (2) a carbonyl compound such as formaldehyde.

Other preferred polymers according to the invention are condensed from three monomers, namely (1) a monomer selected from compounds having the formula

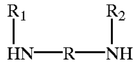

wherein R is >C═NH, —[$(CH_2)_m NH(CH_2)_o$]p— and —$(CH_2)$—$_n$ where m, o, and p are zero or an integer from 1 to 4, and at least one of m or o is an integer, n is an integer from 1 to 6, and $R_1$ and $R_2$ are H or alkyl or alkenyl or acyl or aryl or melamine or guanamine or piperazine, (2) a carbonyl compound such as formaldehyde, and (3) a compound of the formula

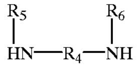

wherein $R_4$ is >C═O or >C═S, and $R_5$ and $R_6$ are H or alkyl.

The following copolymers are especially advantageous for the bioactive compositions of the invention: melamine-guanidine-formaldehyde, melamine-guanidine-urea-formaldehyde, and melamine-guanidine-thiourea-formaldehyde, and melamine-dodecylguanidine-guanidine-formaldehyde.

Other compounds which are useful are melamine-urea-phenylenediamine-formaldehyde, melamine-guanidine-ethylenediamine-formaldehyde, melamine-guanidine-thiourea-glutaraldehyde, melamine-guanidine-1,6-diaminohexane-formaldehyde, melamine-1,6-diaminohexane-formaldehyde, melamine-phyenylenediamine-formaldehyde, melamine-biguanide-formaldehyde, and melamine-biguanide-piperazine-formaldehyde.

Although formaldehyde is the preferred carbonyl compound, it is contemplated that other aldehydes may be used, e.g., glyoxal and glutaraldehyde.

During the polymerization, a cross-linking agent may be added. Such a monomer agent may be any di or poly-functional compound capable of reacting with N-hydroxymethylene groups. The dimensions of the cross-linked structure formed thereby can be varied by varying the dimensions and degree of functionality of the cross-linking agent. The resulting products are in most instance novel polymers. Examples of such polymers include the reaction products of melamine-guanidine-formaldehyde copolymer with an alkylguanidine or its salt such as laurylguanidine acetate (dodine) and 3-(1-methylethyl)-1H-2,1,3-benzothiadiazin-4(3H)-one 2,2-dioxide(bentazone), respectively.

Some examples of such monomeric cross-linking agents are listed in the table below, which is not limiting.

N-hydroxymethylene Reactive Monomers

1. Guanidine
2. Melamine
3. Alkyl primary and secondary amines, for example, methyl amine, dimethylamine, and ethylenediamine
4. Cycloalkyl primary and secondary amines, for example, cyclohexylamine and N-methyl-cycolhexylamine, respectively
5. Arylamines, for example, aniline
6. Phenols, for example, phenol
7. Amidines, for example, laurylguanidine and sulfaguanidine
8. Sulfonamides, for example, 3-(1-methylethyl)-H-2,1,3-benzothiadiazin-4(3H)-one 2,2-dioxide
9. Heterocyclic compounds containing primary or secondary amine groups, for example, 3-amino-1-ethylpiperidine and morpholine, respectively
10. Alkylamides, for example, acetamide and succinic acid diamide
11. Arylamides, for example, benzamide and teraphthalic acid diamide
12. Heterocyclic amides, for example, 2-furoic acid amide and 1-methylnicotinamide iodide
13. 2-Amino-4,6-bis(1-hydroxy-2-trichloroethylamino)-s-triazine
14. Taurine
15. Dyes containing a reactive group, for example, vinylsulfonyl or precursor and monochloro- or dichloro-s-triazinyl
16. Alkoxy aroyl imines Water-solubilizing groups may also be introduced into the polymer. This may, for example, be done by conducting the reaction in the presence of sodium hydroxymethanesulfonate, which, if the carbonyl compound is formaldehyde, may be formed in situ by adding sodium bisulfite or sodium sulfite to the polymerization mixture. Alternatively, such compounds may be added at the end of the copolymerization reaction.

In accordance with the above, and in addition to the new copolymers formed by reacting a melamine-guanidine-formaldehyde polymer with dodine and bentazone respectively, a series of polymeric compositions have been produced as embodiments of the general reaction scheme. These polymers, which are exemplary of what can be made according to the present invention, are shown below.

Copolymers Produced

1. Melamine-guanidine-formaldehyde
2. Melamine-guanidine-urea-formaldehyde
3. Melamine-urea-phenylenediamine-formaldehyde
4. Melamine-guanidine-thiourea-foraldehyde
5. Melamine-guanidine-ethylenediamine-formaldehyde
6. Melamine-ethylenediamine-formaldehyde
7. Melamine-guanidine-1,6-diaminohexane-formaldehyde copolymer
8. Melamine-1,6-diaminohexane-formaldehyde copolymer
9. Melamine-phenylenediamine-formaldehyde copolymer
10. Melamine-biguanide-formaldehyde copolymer
11. Melamine-guanidine-piperazine-formaldehyde copolymer
12. Melamine-guanidine-glutaraldehyde copolymer
13. Melamine-guanidine-urea-glutaraldehyde copolymer
14. Melamine-guanidine-thiourea-glutaraldehyde copolymer
15. Melamine-guanidine-ethylendiamine-glutaraldehyde copolymer
16. Melamine-ethylenediamine-glutaraldehyde copolymer
17. Melamine-guanidine-1,6-diaminohexane-glutaraldehye copolymer
18. Melamine-1,6-diaminohexane-glutaraldehyde copolymer
19. Melamine-guanidine-piperazine-glutaraldehyde copolymer The polymer may be adjusted downward to any pH short of creating macroscopic rigid gel continuums. They may be acidified and dispersed with and by one or more acids to the point of nucleation and near-insolubilization to become precursors for the new dispersoid complexes of this invention. Representative acids useful for protonation of these and other polymers of the same type are listed in the table below, which is not limiting.

Representative Dispersing Acids hydrochloric acid
hydrobromic acid
hypobromous acid
propionic Acid
a,a' dichloropropionic acid
hydroxy acetic acid
citric acid
lactic acid
trans crotonic acid
hydroxamic acid
2,6 pyridine dicarboxylic acid
quinolinic acid
imidazole dicarboxylic acid
maleic acid
malonic acid
pipecolic acid
piperidine 2 carboxylic acid
2,6 pyridine dicarboxylic acid
dipicolinic acid
lipoic acid
thiosulfonic acid
8-hydroxy quinoline-5-sulfonic acid
thiolactic acid
sulfamic acid
3,3' thio dipropionic acid
ammunium sulfamate
glutatione
methionine
phenolic acids As previously described, the polymers are formed by a limited condensation of one or more diamines, diamides, mixed amine-amides, and similar monomers, with a carbonyl compound such as formaldehyde. Normally, condensation progresses only to a mean state of oligomerization in which, for example, the polymer molecules are composed of from 10 to 60 monomer units. Preferably, the polymer is formed under alkaline conditions to form a so-called syrup. If desired, the polymer may be acidified to the point of near-insolubilization, at which point a colloidal, basic anion-active copolymer has been obtained.

The conditions under which polymerization/condensation is effected are not critical. Practical considerations make temperatures ranging from ambient to 100° C. desirable. Similarly, the pH may vary being acid, neutral or alkaline, depending upon the reactivity of the monomers, although a alkaline pH is preferred. The reaction may be terminated after as short a time as a few minutes, depending upon the monomers and their ratios and the other conditions.

The polymers of this invention are preferably prepared by forming a mixture of the monomers to be reacted in an aqueous medium suitable for maintaining particles of the polymer in dispersion, condensing the mixture at a temperature broadly from 65 to 80° C., particularly from 68 to 75° C. and typically at from 72 to 74° C. The reaction is continued for a time sufficient to cause the condensation polymerization of the components, but not sufficient to cause aggregation and resin formation. The reaction may take place in standard laboratory or industrial polymerization equipment known in the art.

The pH of the reaction mixture is desirably controlled in the range of from 9.0 to 11.0 by addition of a suitable base such as sodium hydroxide. In various embodiments, a desirable pH will be obtained by virtue of such nucleophils or bases, e.g. guandine or 1-formylpiperidine as are already present as a monomer or capacitance adding compound. Preferably the pH is maintained in the range of from 10 to 10.5 during the condensation reaction. After the condensation has reached the desired degree, the pH is adjusted to from 6.5 to 10.5.

The ratio of the two or three or more monomers of the reactive mixture may be varied. Typically the ratios between amine plus amide equivalents to carbonyl equivalents is about 1.6/1.0.

Although the condensation reaction my be conducted by mixing the monomers together in a reactor with conventional stirring, it is typically useful to preprocess some monomer. This is especially true, for example with melamine which should be finely dispersed, for example, by homogenization in the carbonyl compound, e.g., formaldehyde solution. To avoid formation of solids during reaction, it is especially useful when making, e.g., a melamine-guanidine-formaldehyde polymer, to use all of the melamine and formaldehyde and about 75% of the required amount of guanidine hydrochloride for homogeneous preprocessing. When the mixture is at about 60° C., it is transferred to a preheated reaction vessel and heating is continued to about 70° C. The balance of guanidine hydrochloride is then treated with an equimolar amount of cold aqueous sodium hydroxide to form a slurry, which is then added to the reaction mixture. Addition of various materials to control conditions, e.g., triethanolamine to quickly raise the temperature of the preprocessing mixture, also is useful.

Control of the extent of polymerization may be effected with a scavenger. Various scavengers may be employed. These include such inorganic compounds reactive with the carbonyl compound, such as ammonium hydroxide and hydrogen peroxide. If desired, a Lewis Base scavenger, for example, cyanoquanidine or thiourea or other strong nucleophilic species may be employed to complex with carbonyl monomer. This form of scavenging has the additional benefit of producing complex adjuncts which may further increase the bioactivity of the present compositions. An analogous incorporation of complex adjuncts may be obtained through the addition of such conventional bioactive metal salts as cupric chloride and silver nitrate.

The size of the polymers of this invention will be less than 2000 nm. In general, it has been found that smaller polymer sizes are even more effective. More specifically, polymer under 1000 nm and preferably those under 500 nm and most preferably those under 100 and even 50 nm will exhibit the most advantageous bioactivity.

The compositions of the invention are formed upon coordination complexing of one or more of the foregoing polymers with a capacitance adding compound. By the terms, "capacitance adding compound" or "CAC", it is meant to include dielectric compounds having a specific inductive capacity. These CAC's possess a dielectric constant lower than that of water (78.3 at 25° C.) and imbue the polymer with which they are complexed with capacitance.

These CAC's are dipoles which operate as electron donors inside the complex with hydrous polymer and thereby introduce their specific electronic permittivity through interaction with, and as an opposing potential force to, the positively charged polymer protons. These electrons are desirably provided by the CAC though a highly electronegative group or atom having at least one free pair of electrons. Preferred examples are oxygen (as in an alcoholic group) or sulfur (as in a sulfhydryl group), although halogens may also be employed. In order to properly function in this manner, a CAC is desirably at least hydrophlic, or amphipathic, so that water bound to the polymer is fully incorporated into the coordinated complex. Under these conditions, maximum molecular and ionic depolarization of the complexed composition and increased bioactivities are achieved.

The electrical charge distribution characteristics of the CAC's are most important in relation to forming the subject complexes via bonding to the cationic sites of the polymer particles. To form stable copolymer-CAC complexes, a unit volume of the CAC desirably comprises a dipole with a moment in relation to the cationic force. This allows the CAC to compete with the dipole moment of a unit volume of water entrained with the polymer. Consequently they ordinarily have a dipole moment greater than water (1.87) and preferably greater than 2.0.

It has been found that in order to produce the desired electronic permittivity in the present complexes, the CAC should possess a high effective electrostatic factor (E.F.). Most desirably, suitable compounds have an E.F. greater that 7 and more desirably greater than 30. They may be as high as 550 (e.g. 488 for N N-dimethylformamide, a representative dipolar aprotic CAC). Similarly, the preferred CAC's have a dielectric constant less than 78, more preferably less than 55, at ambient temperature.

With these characteristics a unit micro-volume of CAC can approach the polymer to orient its negative groups as an opposite force to the polymer's cationic force and corresponding volume. This permits formation of the desired coordination complex and creates the capacitance resulting in the enhanced bioactivity of the present invention.

This does not, however, mean that a compound must exhibit all of these enumerated characteristics to be a useful capacitance adding compound. Quite commonly, compounds meeting some, but not all of them may be combined with a complimentary CAC satisfying others. For example, CAC's which are oils having on E.F. less than 7 can be mutually conjugated with a CAC which provides a relatively high E.F. component, e.g. between E.F. 125 and 550. Analogously, a solid silica CAC and a liquid CAC with a high dipole moment can coordinate to form mutually potentiating polymer-CAC coordinated complexes. Thus a composite CAC may be obtained which will coordinate and complex with polymer to provide the specific electrical permittivity desired for the present complexes.

In some instances, the efficacy of a desirable low dielectric compound as a CAC is impaired because of its essentially hydrophobic character. Suitable examples are halocarbons such as 1,1,2-trichloro-1,2,2-trifluorethane; hydrocarbons such as cyclohexane, paraffin oils, aromatics; silicones or solids such as silicas. The advantages of such compounds can, however, be enjoyed by employing them as adjuncts in admixture with other CAC's which are both at least partially hydrophilic and miscible with them.

Because the CAC should not adversely affect the polymer, it should be basic or essentially neutral. CAC's exhibiting a pH greater than 5.5, more desirably greater than 7, are preferred. They help to buffer the dispersion, maintaining the charges and molecular configuration of the particles of complex.

As may be seen from the below table of desirable capacitance adding compounds, myriad compounds and materials will form the present complexes with polymer.

Representative Capacitance Adding Compounds

Diols
1,2 propylene diol
1,3 propylene diol
1,3 butane diol
1,5 pentane diol
1,6 hexane diol
1,3 hexane diol
triethylene glycol
2-ethyl-1,3, hexane diol
Amino Diols
2-amino-2Hydroxymethyl-1,3-propane diol
Triols
glycerol
diglycerol
polyglycerols
thioglycerol
polyglycols
Amides
1-formyl piperidine
diethyl toluamide
dimethyl formamide
coconut diethanolamide condensates
Ethers
ethylene glycol dimethyl ether
ethylene glycol diethylether
diethylene glycol dimethyl ether diisobutylphenoxy/polyethoxy ethanol
mono-para-(1-,4,3,3tetra methylbutyl)phenyl esters of polyglycols
ethylene oxide adducts of nonylphenyl ether
dodeca ethylene glycol mono-laurate
Esters
Sorbitol fatty acid esters
diethylene glycol monolaurate
glycerol monolaurate
diethylene glycol monolaurate
capric/caprilic triglyceride
Alkanolamines
diethanol amine
triethanol amine
triisopopanolamine
2amino 2ethyl propane doil
1,3 diethyl amino ethanol
dimethyl amino ethanol
morpholine
n-propyl alkanolamine
n-propyl ethanolamine
n-buryl diethanolamine
n-methyl diethanolamine
n-propyll diethanolamine-octanoates
n-methyl ethamolamine- oleate
Sugars
sucrose
fructose
Soaps/Surfactants
ethanolamine-propionate
ethanolamine-laurate
isopropanolamine-propionate
isopropanolamine myristate
isopropanolamine-laurate
palmityltrimethyl ammonium chloride
Miscellaneous
nicotine
silicone oil
paraffin oil
silica Preferred CAC's are selected from the group consisting of dihydric and polyhydric alcohols, polyglycols, and derivatives thereof such as their monomethyl ethers. Specific examples are 1,2-propyleneglycol, 1,3-propylene glycol, 1,5-pentanediol, polyethylene glycol, ethylene glycol monomethyl ether, sorbitol, glycerol, diglycerol, sucrose, and glucose. Some of the results of forming this complex are to reduce particulate size and to stabilize the polymer. More importantly however, in forming the complex the CAC preserves and/or more usually magnifies the bioactivity of the uncomplexed polymer.

A desirable property of the CAC and the polymer is that they be compatible with the ultimate vehicles in which the coordinated complex is incorporated. Normally the CAC can be selected with this in mind. Alternatively a mutually miscible solvent, desirably another CAC, is employed to ensure physical compatibility. In addition, the CAC may be selected so as to provide desirable properties to the final product, such as lubricity, emolliency, viscosity, and to help stabilize the finished product.

Propylene glycol is a preferred CAC of the complexes prepared according to the invention, i.e., dispersions prepared and adjusted to an alkaline pH. 1,5-Pentanediol is a preferred stabilizer of alternate dispersions which are formed under alkaline conditions and subsequently acidified to a pH of 3.0 to 6.0 and thereafter adjusted to an alkaline pH. Polyethylene glycol (PEG-400) is also a satisfactory CAC for polymer.

Preferably from 5 to 50 percent by weight of CAC based on the dispersion solids with which they are employed and typically from 25 to 35 percent by weight, are most effective to enhance the stability and activity of the dispersed, complex system.

In a further embodiment of the invention, the present coordinated complex of polymer-CAC is further combined with an inorganic dielectric material. These inorganic dielectric materials are also usually finely particulate solids, preferably being no larger than 500 nm, most preferably less than 100 nm. Suitable examples include silica gel, silica (preferably fumed silica), zeolite and alkali metal carbonate.

This embodiment including an inorganic dielectric material has the benefit of permitting the conversion of the present systems into a stable solid form. Moreover, these solids are readily redispersed in liquid, preferably aqueous, medium for ultimate use. Indeed, where an alkali metal carbonate is employed, aqueous redispersion occurs essentially instantaneously. Finally, it has been discovered that such an inorganic dielectric material can greatly magnify the bioactivity of the present compositions. Consequently, this embodiment is a particularly preferred aspect of this invention.

It is believed that the unusually effective bioactive properties of the present coordinated complex systems are due in part to the following:

1. Protection, by the CAC, of the active sites of the polymer from premature depletion through reaction with random ions when remote from the electrostatic fields of target microorganisms.
2. Extension of the electrical field boundary of the cationically-charged copolymer, which assists the antimicrobial effect by interacting with the oppositely charged fields of the microogranism.
3. Size and geometry, which are such as to permit a proper fit of the systems at the target cells.
4. Competitive inhibition of carbon dixoide respiratory mechanisms in microoganisms requiring carbon dioxide for their existence.
5. Regulation of ionic conductivities adjacent to the cell wall of the target microogranism by the combined effect of added capacitance and of electron transport effect of dielectric current-coupling at the cell.

These properties were among the original objectives of this invention. The theoretical explanations, however, should not be considered as exhaustive or binding.

The complexes of the present invention exhibit particle sizes essentially the same or smaller than those of the polymer from which they are formed. Their size distribution is also remarkable. Commonly, the particles differ little in size with substantially all being within a narrow range of less than 100, preferably 50 and most preferably 20, nanometers.

The particulate dispersions of polymer—CAC complex can be incorporated within a variety of known vehicles to form desired end use products. Such vehicles may be those typically used in antimicrobial/deodorant soap bars, antimicrobial/deodorant detergent bars, liquid soaps, deodorants, surgical scrubs, antimicrobial personnel handwashers, preoperative skin preparations/skin degreasers, shampoos, light duty detergents, sanitizers, premoistened tissues, and the like.

By way of illustrating product uses, the present dispersions may be used as components of solid or liquid soaps, including alkali metal, ammonium, amine, and metallic soaps, e.g., aluminum soaps. Typical vehicles used in surgical scrubs and antimicrobial personnel handwashers include non-ionic and anionic surfactants. Typical vehicles for use in cosmetic bases include water-in-oil emulsions, such as cold cream, and oil-in-water emulsions, such as vanishing cream.

Because of their high degrees of dispersion and dispersability, the present particles may be delivered in mists, droplets, aerosols and vapors, e.g., to sanitize hard surfaces. Additional contemplated uses are preservatives for personal care products, e.g., creams, ointments, shampoos, and shaving preparations, and preservatives for metal-working products, machine tool coolants and cutting oil emulsions. The dispersions can be formulated with non-ionic, anionic, amphoteric, and cationic surfactants.

The present dispersions may be incorporated in cellulosic substrates to render them antimicrobial. Similarly, microporous plastic films may serve as substrates for carrying the antimicrobial copolymers. The cationic nature of the polymers is expected to render them substantive to cellulose and application at pH's slightly below 7 may be advantageous.

Virtually any kind of vehicle which is chemically and dimensionally compatible with the polymeric CAC system may be used. Aqueous vehicles are most common. Representative examples are agrochemicals, microbiocides, detoxicants, dyes, isotopically labelled substances, and if toxicology and pharmacology of the dispersoid system are suitable, drugs for ingestion or systemic use.

It has been found that the dispersions of this invention have extremely good antimicrobial properties. In some instances, application of the colloidal dispersions has resulted in rapid kills of $10^6$–$10^7$ cells/ml. For example, within 10 minutes 500 ppm of a syrup based on melamine-guanidine-formaldehyde polymer complexed with propylene glycol reduced an inoculum of about $1.5\times10^7$ cells/ml of *Staphylococcus aureus* ATCC 6538 to 10 cells/ml, and no cells were recovered after 20 minutes.

Importantly, the antimicrobial properties of the present systems are not affected by hard water. Thus, the bactericidal effectiveness of a preferred complex derived from melamine, guanidine, and formaldehyde polymer in association with propylene glycol as he CAC, was identical in hard water as in soft water (99.999+% reduction of *Staphylococcus aureus* ATCC 6538 within 30 seconds using an inoculum of $10^6$ CFU/ml.).

The complexes of this invention can be made by first preparing the polymer dispersion and thereafter introducing an effective amount of CAC. Alternatively, these complexes can be prepared by adding the CAC to the condensation mixture prior to or during the polymerization reaction.

As an alternative to the preparation of polymer which is formed and maintained under alkaline conditions, a condensate formed under alkaline conditions may be acidified by adjusting the pH of the condensation mixture to a pH of from 3.0 to 6.0 in order to acidify the polymer condensate short of formation of solid resin gel continuum. Thereafter, the pH of the acidified dispersion is adjusted to from 6.5 to 10.5. Acidification, preferably in the presence of CAC as defined above, is conducted by introducing a suitable acid to the polymer condensate, thereby reducing the pH to preferably from 3.0 to 6.0 for under about 10 minutes. Such an acid is one whose pK and structure are such as to protonate and disperse the polymer, while acidifying the complex. Thereafter the pH is raised by addition of a base or buffer, desirably to from 7.0 to 9.5.

It has also been discovered that by performing a homogenous, partial acidification e.g., to about pH 5.5, the CAC and the cationic functional groups on the hydrous polymer simultaneously become oriented. Their planar surfaces form a multiphase sequence of conjugated surfaces. The electronegative atoms of the CAC then couple firmly to the basic catonic groups of the polymer providing a structural and electrical organization active in the microenvironment of cells.

The monomers listed in the table below all share a planarity which contributes to this desired symmetry. Polymer containing these monomer groups facilitates formation of a stable coordinated complex. Although it is preferred that at least one monomer be planar or near-planar, planarity is not a requirement of this invention in its broader aspects. However, it is believed that the planar or near-planar monomers make an important contribution to the geometry of the polymer which, together with the dielectric CAC and the size of the resulting bioactive dispersoid system, permit proper conformation with the analogous molecular structures of the organisms upon which they act.

A wide variety of planar or near-planar monomers may be employed. Representative generic classes are listed in the Table below which is not limiting.

Representative Classes of Planar Or Near-Planar Monomers

| | |
|---|---|
| 1. s-Triazines | 12. Acridines |
| 2. Purines | 13. Naphthalenes |
| 3. Carbazoles | 14. Anthracenes |
| 4. Pyridines | 15. Anthraquinones |
| 5. Pyrimidines | 16. Benzenes |
| 6. Imidazoles | 17. Orotic acids |
| 7. Thiaxoles | 18. Thioorotic acids |
| 8. Pyrazoles | 19. Barbiturates |
| 9. Piperazines | 20. Hydantoins |
| 10. Thiadiazoles | 21. Furans |
| 11. Quinoxalines | 22. Thiophenes |

The compositions of the present invention may make use of buffers to set and maintain a desired pH. Many such buffers are described in U.S. Pat. No. 3,016,327, the disclosure of which is incorporated herein by reference. The following table show exemplary preferred organic buffers and the pH range within which they desirably operate.

| | |
|---|---|
| Triethanol amine | 7.2–9.1 |
| Tromethamine/Citric Acid | 7.2–9.5 |
| Piperazine HCl | 4.6–10.6 |
| Imidazole | 6.2–7.8 |
| Hystidine | approx. 7.6 |
| Lysine | approx. 9.7 |
| Glycine | approx. 10.8 |

Although this invention focuses on the bioactivity of the present coordinated complexes, it is important to appreciate that the polymers alone exhibit an important bioactivity. Unfortunately, these polymers are ordinarily unstable in that their bioactivity declines fairly quickly over time. Nonetheless, there are obviously instances in which the polymer precursors to the present complexes are themselves useful for antimicrobial and similar applications.

As has already been described, upon complexing with CAC, the activities of these polymers is stablized. This alone establishes the usefulness of the present invention. However, the result of coordination complexing is by no means so limited. The effect of complex formation is also to potentiate the polymer so as to yield a composition having a bioactivity which may be exponential to that of the polymer alone. Accordingly, those coordinated complexes offer an advance which in many instances is magnitudinal over the products of the prior art.

As a further guide to the practice of this invention, the table which follows lists preferred monomer for condensation.

s-Triazine Monomers

1. Melamine
2. Melan,
3. Melem
4. Melon
5. Ammeline
6. Silver nitrate and silver complexes of melamine
7. 2,4-Diamino-6-nitriloamino-s-triazine 2,4-Diamino-6-(p-nitrophenylsulfonamido)-s-triazine 9. Monoalkylisomelamines, for example, 1-allylisomelamine
10. 2,4-Diamino-6-formylamino-s-triazine
11. 2,4,6-Tris(hydrazino)-s-triazine
12. Condensation product of melamine and glucose
13. Ethylenedimelamine
14. Diethylenetrimelamine
15. Trimethylolmelamine
16. Halogenated melamines, for example, 2-(N-chloro) melamine
17. Guanylmelamines, for example:
    A. 3-Phenylguanylmelamine
    B. 3-Methyl-3-phenylguanylmelamine
    C. p-Sulfamyl-3-phenylguanylmelamine
    D. 3-Benzylguanylmelamine
    E. 3-Cyclohexylguanylmelamine
    F. 3-Dodecylguanylmelamine
    G. 3-(p-Chlorophenyl)guanylmelamine
    H. 3-Butylguanylmelamine
    I. 3-(p-Trifluoromethylphenyl)guanylmelamine
18. 2-Amino-4,6-bis(2-hydroxyethyl)-s-triazine
19. 2,4 Diamino-6-(2-hydroxyethyl)-s-triazine
20. 2,4-Diamino-6-uriedo-s-triazines, for example, 2,4-diamino-6-(3-methylureido)-s-triazine
21. 2,4-Diamino-6-thioureido-s-triazines, for example, 2,4 diamino-6-(3-methylthioureido)-s-triazine
22. 2,4-Diamino-s-triazine
23. 2-Aceto-4,6-diamino-s-triazine
24. 2,4-Diamino-6-aryl-s-triazines, for example, 4,6 diamino-6-phenyl-s-triazine
25. 2,4-Diamino-6-alkyl-s-triazines, for example, 2,4-diamino-6-methyl-s-triazine
26. 2,4-Diamino-cycloalkyl-s-triazines, for example, 2,4-diamino-6-cyclohexylmethyl-s-triazine 27. 2,4-Diamino-6-sulfanilamido-s-triazine
28. 2-Amino-4,6-bis(hydroxymethylamino)-s-triazine
29. Hexamethylolmelamine
30. 2-Phenyl-4,6-bis(hydroxymethylamino)-s-triazine
31. 2,4-Diamino-6-(4-aminobenzenesulfonamido)-s-triazine
32. 2,4-Diamino-6-bis(allylamino)-s-triazine
33. Condensation product of melamine and p-aminophenol
34. 2,4-Diamino-6-[aminomethylenebis(acetic acid)]-s-triazine
35. 2-Cyclpropyl-4,6-diamino-s-triazine Heterocyclic Amine Monomers other than s-Triazines 1. Adenine
2. Guanine
3. 2-Aminocarbazole
4. 2,7-Diaminocarbazole
5. 2-Aminobenzimidazole
6. 2,6-Diaminopyridine
7. 4,6-Diaminopyrimidine
8. 2,6-Diaminopyrazine
9. 2,8-Diaminophenazine
10. 5,6-Diaminobenzimidazole
11. 2,4-Diamino-5-phenylthiazole
12. 2,5-Diamino-1,3,4-thiadiazole
13. 3-Aminoquinoxaline-2-carboxylic acid amide
14. 2,6-Diaminopurine
15. 2,8-Diaminoacridine
16. Glycarbylamide (1H-imidazole-4,5-dicarboxamide)
17. Thiazolsulfone (Promizole, 5-[(4-aminophenyl) sulfonyl]-2-thiazolamine)
18. Thioguanine
19. 3,5-Diamino-1,2,4-triazole
20. Piperazine
21. Tryptamine Heterocyclic Amide Monomers 1. Maleic hydrazide
2. Barbituric acid
3. Barbital
4. Luminol
5. Dihydroorotic Acid
6. Uracil
7. 5-Aminouracil
8. Thiouracil
9. 5-Aminothiouracil
10. Cytosine
11. Thymine
12. Uric Acid
13. Alloxan
14. Biotin
15. Hydantoin
16. Orotic acid
17. 2-Thioorotic acid
18. Esters of orotic acid, for example, cetyl orotate
19. 2,5-Bis(carbamoyl)-1-ethylpyridinium bromide N-Bis(Hydroxymethyl)amine-Containing Heterocyclic Monomers Other than s-Triazines 1. Dimethylol-N-methyltriazone
2. Dimethylolglyoxal monourein
3. Tetramethylolglyoxal diurein
4. Dimethylolurone Heterocyclic Monomers other than Ring Nitrogen Heterocycles 1. Furan
2. Furfural
3. Thiophene Guanidine and Guanidine-Based Monomers as Salts or as Free Bases 1. Guanidine
2. Cyanoguanidine
3. Sulfaguanidine
4. Glycocyamine
5. N-(2-Guanidinoethyl)-4-methyl-1,2,3,6-tetraliydropyridine
6. [(2,6-Dichlorophenyl)acetyl]guanidine
7. 2-Guanidinomethyl-1,4-benzodioxane
8. Aminoguanidine 9. [(2,6-Dichlorobenzylidine)amino]guanidine
10. 4-Aminobutylguanidine
11. 1,3-Diaminoguanidine
12. Biguanide
13. 1-Butylbiguanide Urea-and Thiourea-Based Monomers 1. Urea
2. Guanylurea
3. 1,3-Diaminourea
4. Phenylurea
5. 1,3-Bis(hydroxymethyl)urea
6. 1,3-Bis(methoxymethyl)urea
7. Thiourea
8. Guanylthiourea
9. 1,3-Diaminothiourea
10. Phenylthiourea
11. 1,3-Bis(hydroxymethyl)thiourea
12. 1,3-Bis(methoxymethyl)thiourea
13. Citrulline
14. Biuret
15. Allantoin Aliphatic Amine Monomers 1. Ethylene diamine
2. Propylene diamine
3. 1, 6-Hexanediamine
4. 2,2'-Dithiobis(ethylamine)
5. Ethylenediaminetetraacetic Acid
6. trans-1,2-Diaminocyclohexane-N,N,N',N'-tetraacetic acid
7. 1,12-Diaminododecane
8. Diaminomaleonitrile
9. Spermine
10. Spermidine Aromatic Amine Monomers 1. Aniline
2. o-, m-, and p-Phenylenediamines
3. 2,4'-Diaminodiphenyl
4. 4,4'Diaminodiphenylsulfone
5. 4,4'-Diaminodiphenylamine
6. 4,4'-Diaminodiphenylmethane
7. 2,7-Fluorenediamine
8. 1,8-Naphthalenediamine
9. 1,4-Diaminoanthraquinone Amino Acid Monomers 1. Arginine
2. Asparagine
3. Cystine
4. Glutamine
5. Histidine
6. Hydroxylysine
7. Lysine
8. Tryptophan Amino Acid Ester Monomers Esters, for example, methyl esters of:
1. Arginine
2. Asparagine
3. Cystine
4. Glutamine
5. Histidine
6. Hydroxylysine
7. Lysine
8. Tryptophan Amino Acid Amide Monomers I. Amino-Substituted Monocarboxylic Acid Amides A. Amides Derived from the Following Monoaminocarboxylic Acids 1. Alanine
2. Cysteine
3. 3,5-Dibromotyrosine
4. 3,5-Diiodotyrosine
5. Glycine
6. Hydroxyproline
7. Isoleucine
8. Leucine
9. Methionine
10. Phenylalanine
11. Proline
12. Serine
13. Threonine
14. Thyroxine
15. Tyrosine
16. Valine
17. β-Alanine
18. 4-Aminobutyric Acid
19. Anthranilic Acid
20. 4-Aminobenzoic Acid
21. 3-Amino-2-naphthoic Acid
22. 4-Aminosalicylic acid
23. 6-Aminonicotinic Acid
24. Norleucine B. Amides Derived from the Following Diaminocarboxylic Acids 1. Arginine
2. Asparagine
3. Histidine
4. Hydroxylysine
5. Lysine
6. Tryptophan II. Amides Derived from the Following Amino-Substituted Di-carboxylic Acids (Mono- or Di-Amides)

1. Aspartic Acid
2. Cystine
3. Glutamic Acid
4. Glutamine
5. Hydroxyglutamic Acid Aromatic Amide Monomers 1. O-Phthalic acid diamide
2. Isophthalic acid diamide
3. Terephthalic acid diamide
4. 1,8-Naphthlanedicarboxylic acid diamide Aliphatic Amide Monomers Other than those Derived from Aminodicarboxylic Acids 1. Oxamide
2. Malonamide
3. Adipamide
4. Fumaric acid diamide
5. Itaconic acid diamide
6. Glutaconic acid diamide (cis-and-trans-)

Phenolic Monomers

1. Phenol
2. o-, m-, and p- Cresol 3. o-, m-, and p- Chlorophenol
4. 2,4- Dimethylphenol
5. Resorcinol
6. Phloroglucinol
7. 1-Naphthol
8. 2-Naphthol
9. 4-Hydroxyphenylacetamide
10. Ethyl 4-hydroxyphenylacetate
11. Phenolsulfonic acids
12. Octadecylphenolsulfonic acids Sulfonamide Monomers 1. Sulfanilamide
2. Protonsil [4-(2',4'-Diaminophenylazo) benzenesulfonamide]
3. Marfamil (4-Aminomethylbenzenesulfonamide)
4. 5-Amino-2-naphth[1.8-cd]isosulfonazole
5. Sulfamide Polymers as Monomers 1. Peptides
2. Proteins
3. Polyurethanes
4. Phenol-aldehyde polymers
5. Polyamides
6. Polyureas
7. Polyacrylamides
8. Poly(N-hydroxymethylacrylamide)
9. Lignosulfonates Miscellaneous Monomers 1. Cyanamide
2. Sodium cyanamide
3. Dicyandiamide
4. Acrylamide
5. Alkylacrylamides, for example, methylacrylamide
6. 1,2-Cyclohexanedicarboxylic acid diamide
7. N-hydroxymethylacrylamide The inventions are further described in the following examples.

EXAMPLE I

Preparation of a Colloidal Dispersion of Melamine/Guanidine/Formaldehyde Complex At ambient temperature, a mixture of 518.0 g. (4.11 moles) of melamine, 456.4 g. (4.78 moles) of guanidine hydrochloride, 1250.6 g. (15.41 moles) of 37% formalin, 106.9 g. of propylene glycol, and 8.8 g. of 20% aqueous sodium hydroxide was processed for three minutes in a Waring blender, during which time the temperature rose to 60° C. The mixture was then transferred to a resin flask preheated to 74° C. and fitted with a stirrer, condenser, thermometer, port for introducing a means of determining pH, and heating mantle. An additional 13.8 g. of 20% sodium hydroxide was added, and heating was continued. At about pH 9 and when the reaction temperature reached about 67° C., a cold slurry of 153.3 g. (1.60 moles) of guanidine hydrochloride and 233.9 g. (1.58 moles) of aqueous 27% sodium hydroxide was added over a period of eight minutes. 11.3 g. of water was used for rinsing the vessel containing the guanidine slurry. The pH rose briefly to 11.5. During the course of about two and one-half hours following the addition of the guanidine slurry, the temperature was held at about 71° C. and the pH was maintained at 9.5–10.5 by incremental additions of a total of 84.1 g. of 20% aqueous sodium hydroxide. The clear solution was cooled in an ice bath to room temperature. The final pH was 9.0. Unreacted formaldehyde amounted to 0.94% of the mixture. The molar ratio of melamine/guanidine/formaldehyde, based on the reaction mixture, was 1/1.55/3.75.

To 350.2 g. of the above copolymer "syrup" there was added 188.8 g. of propylene glycol and 12.92 g. of concentrated ammonium hydroxide. After 7 weeks, the pH was 7.85. The final product contained 24.1% polymer, 36.6% propylene glycol, and 29.8% water.

Microbiocidal Tests

An amount of complex such as to provide 500 ppm (0.05%) of polymer and like amounts of triclocarban, N-(4-chlorophenyl)-N'-(3,4-dichlorophenyl) urea, and triclosan, 5-chloro-2-(2,4-dichlorophenoxy) phenol, the active antimicrobial compounds used in deodorant soaps, were tested at 35° C. using standardized procedures. Stock solutions of triclocarban and triclosan were made with dimethylformamide and propylene glycol, respectively. Microbiologically suitable deionized water was used for the polymer. Subsequent dilutions of all materials were made with microbiologically suitable deionized water. DE neutralizer broth was used to neutralize the actives before plating and incubating. The results are given in Table 1.

TABLE 1

Microbiocidal Effectiveness of Complex Polymer vs. Triclocarban and Triclosan

| | Test | Number of Recovered Cells/Ml After Indicated Contact Times Contact Time in Minutes | | | | |
|---|---|---|---|---|---|---|
| Microorganism | Material | 0.5 | 5 | 10 | 20 | 30 |
| *Staphylococcus* | Water Control | $1.82 \times 10^7$ | $1.70 \times 10^7$ | $1.48 \times 10^7$ | $1.48 \times 10^7$ | $1.45 \times 10^7$ |
| *aureaus* | Complex | $4.0 \times 10^3$ | $1.1 \times 10^2$ | 20 | <10 | <10 |
| ATCC 6538 | Triclocarban | $1.3 \times 10^7$ | $1.4 \times 10^7$ | $1.46 \times 10^7$ | $1.57 \times 10^7$ | $1.75 \times 10^7$ |
| | Triclosan | $9.0 \times 10^5$ | $2.0 \times 10^3$ | 60 | 20 | <10 |
| *Staphylococcus* | Water Control | $1.6 \times 10^6$ | $1.8 \times 10^6$ | $2.3 \times 10^6$ | $1.9 \times 10^6$ | $2.3 \times 10^6$ |
| *epidermidis* | Complex | $2.14 \times 10^5$ | $2.1 \times 10^4$ | $1.8 \times 10^3$ | $1.5 \times 10^2$ | <10 |
| ATCC 17917 | Triclocarban | $7.0 \times 10^5$ | $5.0 \times 10^5$ | $6.0 \times 10^5$ | $1.1 \times 10^6$ | $1.0 \times 10^6$ |
| | Triclosan | $5.0 \times 10^4$ | $9.0 \times 10^3$ | $2.83 \times 10^3$ | $1.03 \times 10^3$ | $6.7 \times 10^2$ |

TABLE 1-continued

Microbiocidal Effectiveness of Complex Polymer vs. Triclocarban and Triclosan

| Microorganism | Test Material | Number of Recovered Cells/Ml After Indicated Contact Times Contact Time in Minutes 0.5 | 5 | 10 | 20 | 30 |
|---|---|---|---|---|---|---|
| *Escherichia* | Water Control | $1.6 \times 10^7$ | $1.41 \times 10^7$ | $1.54 \times 10^7$ | $1.33 \times 10^7$ | $1.50 \times 10^7$ |
| *coli* | Complex | $3.8 \times 10^6$ | $2.0 \times 10^4$ | $7.9 \times 10^2$ | 40 | 30 |
| ATCC 11229 | Triclocarban | $1.47 \times 10^7$ | $1.25 \times 10^7$ | $1.65 \times 10^7$ | $1.35 \times 10^7$ | $1.81 \times 10^7$ |
| | Triclosan | $1.35 \times 10^7$ | $1.15 \times 10^7$ | $1.10 \times 10^7$ | $1.14 \times 10^7$ | $1.05 \times 10^7$ |
| *Pseudomonas* | Water Control | $7.3 \times 10^6$ | $6.5 \times 10^6$ | $1.09 \times 10^7$ | $1.55 \times 10^7$ | $1.85 \times 10^7$ |
| *aeruginosa* | Complex | $8.0 \times 10^5$ | $4.8 \times 10^4$ | $1.4 \times 10^4$ | $1.4 \times 10^3$ | $3.6 \times 10^2$ |
| ATCC 10145 | Triclocarban | $7.1 \times 10^6$ | $5.2 \times 10^6$ | $8.1 \times 10^6$ | $6.7 \times 10^6$ | $6.7 \times 10^6$ |
| | Triclosan | $5.5 \times 10^6$ | $4.6 \times 10^6$ | $6.9 \times 10^6$ | $3.3 \times 10^6$ | $4.5 \times 10^6$ |
| *Candida* | Water Control | $3.1 \times 10^4$ | $3.5 \times 10^4$ | $4.2 \times 10^4$ | $3.3 \times 10^4$ | $2.8 \times 10^4$ |
| *albicans* | Complex | $1.4 \times 10^4$ | <10 | <10 | <10 | <10 |
| ATCC 10231 | Triclocarban | $1.6 \times 10^4$ | $1.4 \times 10^4$ | $1.3 \times 10^4$ | $1.9 \times 10^4$ | $2.6 \times 10^4$ |
| | Triclosan | 20 | <10 | <10 | <10 | <10 |

The data indicate that triclocarban was virtually ineffective against all five microorganisms used. The polymer dispersion was considerably more effective than triclosan, with the exception of *Candida albicans,* toward which both were equally effective.

The particle size of polymers prepared substantially as described in Example I has been determined by photon correlation spectroscopy using a Coulter N4 Submicron Particle Analyzer. The programmed analysis treats all particles as spheres. The day after manufacture, for example, a copolymer essentially identical to that described above exhibited, in triplicate determinations, a cumulant mean of 33.6 nm. After eight months of standing at ambient temperature, a melamine/guanidine/formaldehyde copolymer also essentially identical to that described above and which was stabilized with propylene glycol, was still clear and fluid. The polymer was measured for particle size by photon correlation spectroscopy. The mean of duplicate determinations of the cumulant mean was 751 nm.

This copolymer complex was evaluated for bactericidal activity at 35° C. and a polymer concentration of 500 ppm (0.05%) with the following results:

TABLE 2

Microbiocidal Effectiveness of a Copolymer With a Cumulant Mean Particle Size of 751 nm

| Microorganism | Test Material | Number of Recovered Cells/Ml After Indicated Contact Times Contact Time in Minutes 0.5 | 5 | 10 | 20 | 30 |
|---|---|---|---|---|---|---|
| *Staphylococcus* | Water Control | $1.45 \times 10^7$ | $1.11 \times 10^7$ | $1.45 \times 10^7$ | $1.68 \times 10^7$ | $1.15 \times 10^7$ |
| *aureus* | Complex | $1.3 \times 10^6$ | $5.0 \times 10^3$ | $1.19 \times 10^3$ | 20 | <10 |
| ATCC 6538 | | | | | | |
| *Escherichia* | Water Control | $1.53 \times 10^7$ | $1.60 \times 10^7$ | $1.71 \times 10^7$ | $1.93 \times 10^7$ | $1.73 \times 10^7$ |
| *coli* | Complex | $1.3 \times 10^7$ | $3.7 \times 10^6$ | $1.3 \times 10^6$ | $1.8 \times 10^5$ | $3.4 \times 10^4$ |
| ATCC 11229 | | | | | | |

Comparison of these data with those in Table 1 shows that the larger sized copolymer is still quite active, although not as active as a copolymer with a smaller particle size.

Example IA

The effect of acidifying a copolymer, then restoring it to a somewhat alkaline pH, was determined and is described in this Example. 350.6 g. of the copolymer syrup whose preparation was described above was acidified with a solution of 35.4 g. of 18.5% aqueous hydrochloric acid and 80.6 g. of 1,5-pentanediol to pH 4.22. The product was then basified to pH 7.73 with a solution of 33.9 g. of 20% aqueous sodium hydroxide in 80.5 g. of 1,5-pentanediol.

Finally, the resulting solution was treated with 12.86 g. of concentrated ammonium hydroxide dissolved in 26.3 g. of 1,5-pentanediol. After 7 weeks, the pH was 8.21. The final product contained 21.9% polymer, 32.3% solvent, and 34.8% water.

Using an amount of product equivalent to 500 ppm (0.05%) of polymer, microbiocidal tests were conducted at 35° C. using the procedure described above. Results are given in Table 3, from which it may be seen that the product was antimicrobial.

TABLE 3

Microbiocidal Effectiveness of An Acidified, Then Basified, Polymer Dispersion

| Microorganism | Test Material | Number of Recovered Cells/Ml After Indicated Contact Times Contact Time in Minutes 0.5 | 5 | 10 | 20 | 30 |
|---|---|---|---|---|---|---|
| *Staphylococcus* | Water Control | $1.82 \times 10^7$ | $1.70 \times 10^7$ | $1.48 \times 10^7$ | $1.48 \times 10^7$ | $1.45 \times 10^7$ |
| *aureus* | Acidified, etc. | $1.13 \times 10^5$ | $5.0 \times 10^2$ | 70 | 30 | <10 |
| ATCC 6538 | Complex | | | | | |
| *Staphylococcus* | Water Control | $1.6 \times 10^6$ | $1.8 \times 10^6$ | $2.3 \times 10^6$ | $1.9 \times 10^6$ | $2.3 \times 10^6$ |
| *epidermidis* | Acidified, etc. | $2.86 \times 10^5$ | $4.5 \times 10^4$ | $1.0 \times 10^4$ | $2.35 \times 10^3$ | $8.9 \times 10^2$ |
| ATCC 17917 | Complex | | | | | |
| *Escherichia* | Water Control | $1.61 \times 10^7$ | $1.41 \times 10^7$ | $1.54 \times 10^7$ | $1.33 \times 10^7$ | $1.50 \times 10^7$ |
| *coli* | Acidified, etc. | $9.3 \times 10^6$ | $4.7 \times 10^4$ | $3.62 \times 10^3$ | $1.8 \times 10^2$ | $1.1 \times 10^2$ |
| ATCC 11229 | Complex | | | | | |
| *Pseudomonas* | Water Control | $7.3 \times 10^6$ | $6.5 \times 10^6$ | $1.09 \times 10^7$ | $1.55 \times 10^7$ | $1.85 \times 10^7$ |
| *aeruginosa* | Acidified, etc. | $1.0 \times 10^6$ | $1.02 \times 10^5$ | $2.1 \times 10^4$ | $4.0 \times 10^3$ | $3.0 \times 10^3$ |
| ATCC 10145 | Complex | | | | | |
| *Candida* | Water Control | $3.1 \times 10^4$ | $3.5 \times 10^4$ | $4.2 \times 10^4$ | $3.3 \times 10^4$ | $2.8 \times 10^4$ |
| *albicans* | Acidified, etc. | $4.0 \times 10^3$ | <10 | <10 | <10 | <10 |
| ATCC 10231 | Complex | | | | | |

EXAMPLE II

Preparation of a Colloidal Dispersion of Melamine/Guanidine/Formaldehyde Complex A mixture of 258.0 g. (2.04 moles) of melamine, 1034.7 g. (10.83 moles) of guanidine hydrochloride, and 1250.4 g. (15.41 moles) of 37% formalin was processed for one minute in a Waring blender, at which time 45.12 g. of triethanolamine was added. With continued agitation, the temperature rose to 64.2° C., and the mixture was added to a preheated (61° C.) resin flask, as described in Example 1. After about seven minutes, the temperature was 68.4° C. There was then added a cold slurry of 156.4 g. (1.64 moles) of guanidine hydrochloride and 235.1 g. (1.59 moles) of 27% aqueous sodium hydroxide, followed immediately by 15.06 g. of triethanolamine. The pH rose to 11.8, then fell. During 2 hours and 50 minutes following the addition of the guanidine slurry, the temperature was held at 72–75° C. The pH was maintained at 9.2–10.8, mostly at 10.2–10.5, by incremental addition of a total of 408.8 g. of 20% aqueous sodium hydroxide. The molar ratio of melamine/guanidine/formaldehyde, based on the reaction mixture, was 1.0/6.11/7.55.

After cooling, 665.3 g. of the very slightly hazy solution was diluted with 332.4 g. of PEG-400 to give a product with a pH of 8.18 and that contained 23.2% polymer, 32.8% PEG-400, and 40.0% water. Using the procedure described in Example 1, the antimicrobial properties of 500 ppm (0.05%) of the complex were determined. Results are shown in Table 4.

TABLE 4

Microbiocidal Effectiveness of Complexed Syrup Comprised of Melamine, Guanidine, and Formaldehyde at a Molar Ratio of 1:6.11:7.55

| Microorganism | Test Material | Number of Recovered Cells/Ml After Indicated Contact Times Contact Time in Minutes 0.5 | 5 | 10 | 20 | 30 |
|---|---|---|---|---|---|---|
| *Staphylococcus* | Water Control | $1.4 \times 10^6$ | $2.0 \times 10^6$ | $3.0 \times 10^6$ | $3.3 \times 10^6$ | $2.7 \times 10^6$ |
| *aureus* | Complex | $2.1 \times 10^2$ | <10 | <10 | <10 | <10 |
| ATCC 6538 | | | | | | |
| *Escherichia* | Water Control | $1.78 \times 10^7$ | $2.57 \times 10^7$ | $2.30 \times 10^7$ | $2.86 \times 10^7$ | $2.91 \times 10^7$ |
| *coli* | Complex | $7.1 \times 10^6$ | $3.46 \times 10^6$ | $2.5 \times 10^4$ | $5.7 \times 10^2$ | 80 |
| ATCC 11229 | | | | | | |

EXAMPLE III

Preparation of a Colloidal Dispersion of Melamine/Guanidine/Thiourea/Formaldehyde Complex A mixture of 518.0 g. (4.11 moles) of melamine, 152.4 g. (1.59 moles) of guanidine hydrochloride, 242.7 g. (3.19 moles) of thiourea, and 1250.4 g. (15.41 moles) of 37% formalin was processed briefly in a Waring blender, then added to a preheated resin flask, as described in Example 1. When the reaction mixture reached 68.4° C., 45.24 g. of triethanolamine was added. Four minutes thereafter there was added a slurry of 152.4 g. (1.59 moles) of guanidine hydrochloride, and 235 g. (1.59 moles) of 20% aqueous sodium hydroxide, followed immediately by 15.14 g. of triethanolamine. The vessel containing the slurry was rinsed into the reaction flask with 16.7 g. of water. Following the addition of the guanidine slurry, the reaction mixture was maintained at 67.9–77.5° C., mostly 74.5–74.8° C., for about 90 minutes, during which time the pH fell from 11.5 to 10.5. The molar ratio of melamine/guanidine/thiourea/formaldehyde was 1.29/1.0/1.0/4.84.

During cooling, the pH fell to 9.81, at which time 118.1 g. of the copolymer mixture was treated with 5.59 g. of a solution consisting of a 1:1 mixture of 18.5% aqueous hydrochloric acid and propylene glycol. The pH was 7.50. After dilution with another 115.6 g. of propylene glycol, the pH was 7.26. When tested against S. aureus ATCC 6538 in the manner described in Example I, after 30 minutes contact at ambient temperature the number of organisms was reduced from $4.57\times10^7$ cells/ml to $1.16\times10^3$cells/ml.

EXAMPLE IV

Combinations of colloidal copolymer complexes according to the invention with a variety of surfactant CAC's were made using the general procedure of adding 8–12% by weight of copolymer to concentrated surfactant, then adding water to achieve a desired concentration. Table 5 describes the results.

TABLE 5

Combination of Complex With Surfactants

| Surfactant Type | Example | Appearance of Initial Mixture | Appearance of Diluted Mixture |
|---|---|---|---|
| Nonionic | Nonoxynol 9 | white cream | clear solution |
| Cationic | Palmityltrimethyl Ammonium Chloride | white cream | clear solution |
| Amphoteric | Cocoamphopropionate | clear solution | clear solution |
| Anionic | Sodium Laureth Sulfate | clear solution | flocculation occurs |

In a similar manner, copolymer- CAC/surfactant combinations are prepared using a sulfosuccinate (disodium ricinoleamido MEA-sulfosuccinate), a glyceryl ester (PEG-30 glyceryl monococoate), a betaine (cocamidopropyl betaine), an organic sulfate salt (triethanolamine lauryl sulfate), and a metallic soap (aluminum tripalmitate/trimyristate dispersion).

The copolymer- CAC/surfactant combinations tabulated and described above, are applicable in a variety of end-products such as cold creams, hand lotions, hair shampoos, rug shampoos, and dishwashing detergents.

EXAMPLE V

A surgical scrub was prepared using 3% of a melamine/guanidine/formaldehyde polymer prepared according to the invention that was acidified then basified, and then combined with propylene glycol, glycerol, and a hydrophilic silica. The surfactant was sodium lauryl sulfate. Coconut diethanolamide was added as a foam booster.

To evaluate the efficacy of this product as a surgical scrub, a glove juice test was conducted in accordance with the recommendations set forth in the Food and Drug Administration's Tentative Final Order on *Over-the-Counter Drugs Generally Recognized as Safe, Effective, and Not Misbranded* (*Federal Register* 43, No. 4, Jan. 6, 1978, pp. 1242–1243). Statistical analysis of the data showed that one minute and one hour after hands were washed with the product under standard conditions, microbial reductions in the glove juice were as much as nearly one log as compared to baseline data.

EXAMPLE VI

An antimicrobial personnel handwash was prepared as follows. To 140 parts by weight of melamine/guanidine/formaldehyde syrup that was acidified then basified, was added one part by weight of a hydrophilic silica. After blending this mixture in a Waring blender, 2650 parts by weight of triethanolamine lauryl sulfate (Bofors Lakeway 101-30) was added, and blending was continued until a homogeneous mixture was obtained.

EXAMPLE VII

A homogeneous antimicrobial shampoo concentrate was prepared in a Waring blender by blending 944 parts by weight of Bofors Lakeway 402-M shampoo concentrate, 0.4 of a part by weight of a hydrophilic silica, and 53 parts by weight of a melamine/guanidine/formaldehyde polymer that was acidified then basified.

EXAMPLE VIII

Soap bars were prepared from a base of 85% tallow, 15% coconut oil and melamine/guanidine/formaldehyde copolymercomplexed with glycerolthat had been acidified then basified. The concentrations of copolymer ranged from 0.75% to 3.5%. Lather was rich and foamy, with an emollient feel.

EXAMPLE IX

Soap bars also were made using 1.5% of copolymer. The syrup had been prepared according to Example I, but the stabilizer was a mixture of glycerol and hydrophilic fumed silica. The final soap composition contained 0.23% of silica.

EXAMPLE X

Additional soap bars were made using 1.5% of an acidified then buffered complex. The polymer was prepared according to Example IA but the stabilizer was a mixture of glycerol and hydrophilic fumed silica. The final soap composition contained 0.16% of silica.

EXAMPLE XI

Syndet bars consisting mainly of nonionic surfactants were made using the ingredients described in Examples IX and X. During handwashing with these bars, the feel was that of a bar soap, not a simple syndet bar without cold-cream.

Example XII

An antibacterial moist towelette is prepared by impregnating nonwoven fabric with a blend consisting of copolymer syrup, glycerol, modified lanolin,, ethyl alcohol and water.

Example XIII

Production and delivery of biocidal copolymer colloidal dispersions in droplets of aqueous mist is carried out as follows. A colloidal dispersion of copolymer complex based on melamine/guanidine/formaldehyde in which the stabilizer was propylene glycol was metered with water into the chamber of an ultrasonic transducer unit. The unit was a T.D.K. Ultrasonic Humidifier whose module was set to oscillate at a frequency of about 4.5 megahertz. The ultrasonic vaporizer generated a mist containing complex which was directed to and caused to condense on hands and on a hard surface.

Following the same procedure, biocidal colloidal mists may be prepared and directed to condense upon the surfaces of plants and harvested crops, to provide both efficient agricultural use of water and the utilities provided by the complex dispersion.

Example XIV

A copolymer complex based on melamine/guanidine/formaldehyde and containing propylene glycol as the stabilizer, was admixed with 3.0% by weight of a hydrophilic precipitated silica (Sipernat 283 LS) to form a stable, thixotropic system.

A similar result was obtained using a copolymer syrup that been acidified, then basified. Propylene glycol was the stabilizer or CAC used to produce this complex upon addition of further silia CAC, a free flow powder was obtained.

What is claimed is:

1. A composition of matter having bioactive properties comprising particles of a coordinated complex of a basic, hydrous condensation polymer of:

(i) carbonyl compound and (ii) a monomer capable of reacting therewith with a capacitance adding compound, said particles being no larger than 2000 nm.

2. The composition of claim 1, wherein the polymer is the further condensate product of a cross-linking monomer capable of reacting with an N-hydroxymethylene group.

3. The composition of claim 2, wherein substantially all the particles of complex are less than 100 nm.

4. The composition of claim 1, wherein the monomer capable of reacting with carbonyl compound is a monomer selected from compounds having the formula:

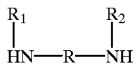

wherein R is >C═NH, $—[(CH_2)_mNH(CH_2)_o]_p—$ and $—(CH_2)_n—$ where m, o, and p are zero or an integer from 1 to 4, and at least one of m or o is an integer, n is an integer from 1 to 6, and $R_1$ and $R_2$ are H or alkyl or melamine or guanamine or piperazine.

5. The composition of claim 2, wherein the monomer capable of reacting with an N-hydroxymethylene group is a compound of the formula:

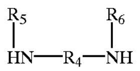

wherein $R_4$ is >C═O or >C═S, and $R_5$ and $R_6$ are H or alkyl.

6. The composition of claim 5, wherein substantially all of the particles of the coordinated complex are less than 100 nm.

7. The composition of claim 6, wherein said polymer is formed from melamine, guanidine, and formaldehyde.

8. The composition of claim 6, wherein said polymer is formed from melamine, guanidine, thiourea and formaldehyde.

9. The composition of claim 6, wherein said polymer is formed from melamine, guanidine, urea and formaldehyde.

10. The composition of claim 6, wherein said polymer is formed from melamine, urea and formaldehyde.

11. The composition of claim 5, wherein the capacitance adding compound possess a dielectric constant of less than 78 and a dipole moment greater than 1.87.

12. The composition of claim 1, wherein said capacitance adding compound is selected from the group consisting of dihydric and trihydric alcohols, polyglycols, and derivatives thereof.

13. The composition of claim 1, wherein the coordinated complex comprises particles combined with a finely divided inorganic dielectric material.

14. The composition of claim 13, wherein the inorganic dielectric material comprises silica having a particle size of less than 100 nm.

15. The composition of claim 13, wherein the inorganic dielectric material comprises alkali metal carbonate having a particle size of less than 100 nm.

16. A method for preparing bioactive composition of matter comprising the steps of:

(a) forming a mixture of (i) a compound of the formula

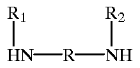

wherein R is >C═NH, $—[CH_2)_mNH(CH_2)_o]_p—$ and $—(CH_2)_n—$ where m, o, and p are zero or an integer from 1 to 4, and at least one of m or o is an integer, n is an integer from 1 to 6, and $R_1$ and $R_2$ are H or alkyl or melamine or guanamine or piperazine and (ii) carbonyl compound in an aqueous medium suitable for maintaining particles of polymer produced from said monomer in dispersion;

(b) condensing said mixture for a time sufficient to cause condensation to a limited degree sufficient to form a hydrous polymer dispersion having particle sizes of less than 2000 nm.;

(c) terminating the polymerization reaction.

17. The method of claim 16, wherein capacitance adding compound is added in an amount sufficient to form a coordinated complex with the polymer.

18. The method of claim 16, wherein the mixture additionally contains a compound of the formula

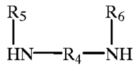

wherein $R_4$ is >C═O or >C═S, and $R_5$ and $R_6$ are H or alkyl.

19. The method of claim 16, wherein the pH of the polymer dispersion is adjusted to from 6.5 to 10.5.

20. The method of claim 16, wherein the capacitance adding compound is selected from the group consisting of dihydric and trihydric alcohols, polyglycols, and derivatives thereof.

21. The method of claim 16, wherein a Lewis base is added to the condensation polymer in an amount sufficient to terminate the polymerization reaction.

22. The method of claim 16, wherein the condensation polymer is subjected to vacuum during the polymerization reaction to reduce the amount of attendant water.

23. The method of claim 21, wherein said vacuum is employed to reduce the presence of carbonyl compound.

24. The method of claim 16, wherein an acid is added in the presence of capacitance adding compound to convert said polymer into complexed, basic-cationic form.

* * * * *